US008124169B2

(12) United States Patent
Ylitalo et al.

(10) Patent No.: US 8,124,169 B2
(45) Date of Patent: Feb. 28, 2012

(54) ANTIMICROBIAL COATING SYSTEM

(75) Inventors: Caroline M. Ylitalo, Stillwater, MN (US); Gerald R. A. Hofmann, Oakdale, MN (US); Mitchell T. Johnson, Gig Harbor, WA (US); Linda K. M. Olson, Saint Paul, MN (US); Duane Douglas Fansler, Dresser, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 686 days.

(21) Appl. No.: 12/097,334

(22) PCT Filed: Dec. 14, 2006

(86) PCT No.: PCT/US2006/047779
§ 371 (c)(1),
(2), (4) Date: Nov. 10, 2008

(87) PCT Pub. No.: WO2007/070649
PCT Pub. Date: Jun. 21, 2007

(65) Prior Publication Data
US 2009/0155451 A1     Jun. 18, 2009

Related U.S. Application Data

(60) Provisional application No. 60/743,037, filed on Dec. 14, 2005, provisional application No. 60/743,038, filed on Dec. 14, 2005.

(51) Int. Cl.
*B05D 5/00* (2006.01)
(52) U.S. Cl. .......................................................... 427/8
(58) Field of Classification Search ........................ None
See application file for complete search history.

(56) References Cited

U.S. PATENT DOCUMENTS

| | | | |
|---|---|---|---|
| 2,449,274 | A | 9/1948 | Broll |
| 2,502,881 | A | 4/1950 | Parker |
| 2,537,124 | A | 1/1951 | Earle et al. |
| 3,832,459 | A | 8/1974 | Berkeley |
| 3,926,830 | A | 12/1975 | Horiguchi et al. |
| 4,070,194 | A | 1/1978 | Arakawa |
| 4,070,510 | A | 1/1978 | Kahn |
| 4,071,645 | A | 1/1978 | Kahn |
| 4,231,370 | A | 11/1980 | Mroz et al. |
| 4,308,625 | A | 1/1982 | Kitko |
| 4,353,866 | A | 10/1982 | Wong |

(Continued)

FOREIGN PATENT DOCUMENTS

AU         4904672         5/1974

(Continued)

OTHER PUBLICATIONS

*The Wiley Encyclopedia of Packaging Technology*, pp. 400-406 (John Wiley & Sons, 1986).

(Continued)

*Primary Examiner* — Erma Cameron
(74) *Attorney, Agent, or Firm* — Nicole J. Einerson

(57) ABSTRACT

An antimicrobial coating system, a film-forming composition, and an antimicrobial film. In some embodiments, the antimicrobial coating system can include a film-forming composition comprising a polymer having an effective molecular weight, and an effective amount of an antimicrobial agent dispersed within the polymer. The film-forming composition can form a water-insoluble, biocidal antimicrobial film when applied to a surface.

19 Claims, 1 Drawing Sheet

U.S. PATENT DOCUMENTS

| | | |
|---|---|---|
| 4,384,869 A | 5/1983 | Wong |
| 4,420,412 A | 12/1983 | Wong |
| 4,441,928 A | 4/1984 | Iijima |
| 4,499,001 A | 2/1985 | Eoga |
| 4,502,605 A | 3/1985 | Wloszczyna |
| 4,578,357 A | 3/1986 | Melpolder |
| 4,584,192 A | 4/1986 | Dell et al. |
| 4,699,885 A | 10/1987 | Melpolder et al. |
| 4,717,671 A | 1/1988 | Melpolder |
| 4,783,340 A | 11/1988 | McDonell et al. |
| 4,793,988 A | 12/1988 | Casey et al. |
| 4,954,544 A | 9/1990 | Chandaria |
| 4,965,063 A | 10/1990 | Casey et al. |
| 5,057,303 A | 10/1991 | Casey |
| 5,064,635 A | 11/1991 | Casey |
| 5,110,492 A | 5/1992 | Casey |
| 5,125,956 A | 6/1992 | Korte et al. |
| 5,154,917 A | 10/1992 | Ibrahim et al. |
| 5,174,995 A | 12/1992 | Davis |
| 5,196,243 A | 3/1993 | Kawashima |
| 5,223,245 A | 6/1993 | Ibrahim et al. |
| 5,234,974 A | 8/1993 | Calhoun et al. |
| 5,288,486 A | 2/1994 | White |
| 5,357,989 A | 10/1994 | Gathani |
| 5,408,022 A | 4/1995 | Imazato et al. |
| 5,409,977 A | 4/1995 | Sitaramiah et al. |
| 5,413,789 A | 5/1995 | Hagiwara |
| 5,418,013 A | 5/1995 | Detrick et al. |
| 5,420,197 A | 5/1995 | Lorenz et al. |
| 5,421,898 A | 6/1995 | Cavanagh |
| 5,454,886 A | 10/1995 | Burrell et al. |
| 5,460,647 A | 10/1995 | Snedeker et al. |
| 5,460,802 A | 10/1995 | Asami et al. |
| 5,460,833 A | 10/1995 | Andrews et al. |
| 5,464,470 A | 11/1995 | Brachman et al. |
| 5,470,585 A | 11/1995 | Gilchrist |
| 5,478,382 A | 12/1995 | Miller et al. |
| 5,482,654 A | 1/1996 | Luttrell et al. |
| 5,489,331 A | 2/1996 | Miller et al. |
| 5,492,558 A | 2/1996 | Miller et al. |
| 5,532,029 A | 7/1996 | Fuerst et al. |
| 5,532,290 A | 7/1996 | Newington et al. |
| 5,547,662 A | 8/1996 | Khan et al. |
| 5,548,010 A | 8/1996 | Franer |
| 5,567,420 A | 10/1996 | McEleney et al. |
| 5,567,753 A | 10/1996 | Shuman et al. |
| 5,569,461 A | 10/1996 | Andrews |
| 5,585,407 A | 12/1996 | Patel et al. |
| 5,586,643 A | 12/1996 | Zabron et al. |
| 5,612,324 A | 3/1997 | Guang Lin et al. |
| 5,667,303 A | 9/1997 | Arens et al. |
| 5,680,962 A | 10/1997 | McEleney et al. |
| 5,681,575 A | 10/1997 | Burrell et al. |
| 5,695,857 A | 12/1997 | Burrell et al. |
| 5,710,141 A | 1/1998 | Lin et al. |
| 5,746,814 A | 5/1998 | Malhotra et al. |
| 5,747,011 A | 5/1998 | Ross et al. |
| 5,753,062 A | 5/1998 | Jansz et al. |
| 5,753,210 A | 5/1998 | McEleney et al. |
| 5,753,251 A | 5/1998 | Burrell et al. |
| 5,766,615 A | 6/1998 | Narayanan |
| 5,770,255 A | 6/1998 | Burrell et al. |
| 5,817,325 A | 10/1998 | Sawan et al. |
| 5,837,275 A | 11/1998 | Burrell et al. |
| 5,849,311 A | 12/1998 | Sawan et al. |
| 5,929,160 A | 7/1999 | Krepski et al. |
| 5,958,383 A | 9/1999 | McEleney et al. |
| 5,958,440 A | 9/1999 | Burrell et al. |
| 5,985,308 A | 11/1999 | Burrell et al. |
| 5,998,431 A | 12/1999 | Tseng et al. |
| 6,007,797 A | 12/1999 | Bell et al. |
| 6,017,553 A | 1/2000 | Burrell et al. |
| 6,024,976 A | 2/2000 | Miranda et al. |
| 6,080,490 A | 6/2000 | Burrell et al. |
| 6,086,858 A | 7/2000 | McEleney et al. |
| 6,102,205 A | 8/2000 | Greff et al. |
| 6,126,931 A | 10/2000 | Sawan et al. |
| 6,146,618 A | 11/2000 | Bell et al. |
| 6,146,651 A | 11/2000 | Kritzler |
| 6,146,654 A | 11/2000 | Kubo |
| 6,150,004 A | 11/2000 | Oikawa et al. |
| 6,170,564 B1 | 1/2001 | Steele |
| 6,197,814 B1 | 3/2001 | Arata |
| 6,238,686 B1 | 5/2001 | Burrell et al. |
| 6,239,048 B1 | 5/2001 | Wilson et al. |
| 6,261,541 B1 | 7/2001 | Karpov et al. |
| 6,264,936 B1 | 7/2001 | Sawan et al. |
| 6,267,590 B1 | 7/2001 | Barry et al. |
| 6,267,976 B1 | 7/2001 | Barnhart et al. |
| 6,290,936 B1 | 9/2001 | Ross et al. |
| 6,296,863 B1 | 10/2001 | Trogolo et al. |
| 6,299,799 B1 | 10/2001 | Craig et al. |
| 6,306,419 B1 | 10/2001 | Vachon et al. |
| 6,306,810 B1 | 10/2001 | Cheung et al. |
| 6,333,093 B1 | 12/2001 | Burrell et al. |
| 6,340,663 B1 | 1/2002 | Deleo et al. |
| 6,342,212 B1 | 1/2002 | Schuette et al. |
| 6,365,130 B1 | 4/2002 | Barry et al. |
| 6,391,226 B1 | 5/2002 | Chauvette et al. |
| 6,454,813 B1 | 9/2002 | Chan |
| 6,462,127 B1 | 10/2002 | Ingrisch et al. |
| 6,467,897 B1 | 10/2002 | Wu et al. |
| 6,482,423 B1 | 11/2002 | Beerse et al. |
| 6,504,583 B2 | 1/2003 | Li et al. |
| 6,544,621 B1 | 4/2003 | Schuette et al. |
| 6,554,156 B1 | 4/2003 | Chong |
| 6,582,715 B1 | 6/2003 | Barry et al. |
| 6,583,176 B2 | 6/2003 | Arata |
| 6,584,668 B2 | 7/2003 | Green et al. |
| 6,613,728 B1 | 9/2003 | Sirianni et al. |
| 6,641,829 B1 | 11/2003 | Green et al. |
| 6,653,522 B1 | 11/2003 | Blumenthal et al. |
| 6,667,082 B2 | 12/2003 | Bamore et al. |
| 6,673,761 B2 | 1/2004 | Mitra et al. |
| 6,677,287 B1 | 1/2004 | Willman et al. |
| 6,726,584 B2 | 4/2004 | Iggulden |
| 6,730,294 B1 | 5/2004 | Kritzler |
| 6,730,654 B2 | 5/2004 | Godfroid et al. |
| 6,733,766 B2 | 5/2004 | Gott et al. |
| 6,741,523 B1 | 5/2004 | Bommarito et al. |
| 6,772,708 B2 | 8/2004 | Klofta et al. |
| 6,802,891 B2 | 10/2004 | Kritzler |
| 6,814,816 B2 | 11/2004 | Achar et al. |
| 6,838,078 B2 | 1/2005 | Wang et al. |
| 6,841,527 B2 | 1/2005 | Mitra et al. |
| 6,884,741 B2 | 4/2005 | Batdorf |
| 6,894,095 B2 | 5/2005 | Russo et al. |
| 6,905,711 B1 | 6/2005 | Tullo et al. |
| 6,911,243 B2 | 6/2005 | Sher et al. |
| 6,916,480 B2 | 7/2005 | Anderson et al. |
| 6,926,745 B2 | 8/2005 | Scheuing et al. |
| 6,951,834 B2 | 10/2005 | Mitra et al. |
| 7,049,367 B2 | 5/2006 | Mazanek et al. |
| 7,053,029 B2 | 5/2006 | MacDonald et al. |
| 7,323,163 B2 | 1/2008 | Wang |
| 2002/0142036 A1 | 10/2002 | Rupprecht |
| 2003/0118733 A1 | 6/2003 | Jackson et al. |
| 2003/0147960 A1 | 8/2003 | Lin et al. |
| 2003/0157147 A1 | 8/2003 | Hoge et al. |
| 2003/0175438 A1 | 9/2003 | Reeve |
| 2003/0191036 A1 | 10/2003 | MacDonald et al. |
| 2004/0043686 A1 | 3/2004 | Batdorf |
| 2004/0044299 A1 | 3/2004 | Utsugi |
| 2004/0137815 A1 | 7/2004 | Ellis et al. |
| 2004/0234561 A1* | 11/2004 | Ansmann et al. ............ 424/401 |
| 2005/0000642 A1 | 1/2005 | Everaerts et al. |
| 2005/0003163 A1 | 1/2005 | Krishnan |
| 2005/0025668 A1 | 2/2005 | Katsigras et al. |
| 2005/0047961 A1 | 3/2005 | Bains et al. |
| 2005/0048856 A1* | 3/2005 | Hauser et al. .................. 442/59 |
| 2005/0065048 A1 | 3/2005 | MacDonald et al. |
| 2005/0080158 A1 | 4/2005 | Ong et al. |
| 2005/0089539 A1 | 4/2005 | Scholz et al. |
| 2005/0095266 A1 | 5/2005 | Perichaud et al. |
| 2005/0101511 A1 | 5/2005 | Zocchi |
| 2005/0129742 A1 | 6/2005 | Bringley et al. |
| 2005/0129766 A1 | 6/2005 | Bringley et al. |

| | | | |
|---|---|---|---|
| 2005/0129929 A1 | 6/2005 | Patton et al. | |
| 2005/0129937 A1 | 6/2005 | Patton et al. | |
| 2005/0137540 A1 | 6/2005 | Villanueva et al. | |
| 2005/0191326 A1 | 9/2005 | Melker | |
| 2005/0227893 A1 | 10/2005 | Johnson et al. | |
| 2005/0233930 A1* | 10/2005 | Cheung et al. | 510/407 |
| 2005/0249791 A1* | 11/2005 | Hobbs et al. | 424/443 |
| 2005/0255016 A1 | 11/2005 | Svendsen et al. | |
| 2005/0272335 A1 | 12/2005 | Johnson et al. | |
| 2006/0008912 A1 | 1/2006 | Simon et al. | |
| 2006/0030512 A1 | 2/2006 | Hart | |
| 2006/0040835 A1 | 2/2006 | Newkirk et al. | |
| 2006/0127425 A1 | 6/2006 | Walls et al. | |
| 2006/0134163 A1 | 6/2006 | Bagwell | |
| 2007/0275101 A1 | 11/2007 | Lu et al. | |
| 2008/0026026 A1 | 1/2008 | Lu et al. | |
| 2008/0095965 A1 | 4/2008 | Paiva et al. | |

FOREIGN PATENT DOCUMENTS

| | | |
|---|---|---|
| DE | 2004019687 | 4/2005 |
| EP | 0 075 934 | 4/1986 |
| EP | 0 549 145 | 6/1993 |
| EP | 0 488 980 | 7/2001 |
| EP | 0 875 146 | 7/2002 |
| EP | 1 400 574 | 3/2004 |
| EP | 1 443 099 | 8/2004 |
| EP | 1 457 529 | 9/2004 |
| FR | 2043995 | 5/1969 |
| GB | 1073462 | 11/1967 |
| GB | 1553132 | 9/1979 |
| GB | 2 372 939 | 9/2002 |
| JP | 60-170674 | 4/1985 |
| JP | 93049712 | 7/1993 |
| JP | 2004-269836 | 9/2004 |
| JP | 2005-319240 | 11/2005 |
| JP | 2006-111815 | 4/2006 |
| JP | 2006-299214 | 11/2006 |
| WO | WO 84/01102 | 3/1984 |
| WO | WO 86/05391 | 9/1986 |
| WO | WO 00/61107 | 10/2000 |
| WO | WO 00/71183 | 11/2000 |
| WO | WO 01/43549 | 6/2001 |
| WO | WO 01/46900 | 6/2001 |
| WO | WO 01/80920 | 11/2001 |
| WO | WO 02/50241 | 6/2002 |
| WO | WO 02/092336 | 11/2002 |
| WO | 03/018732 | 3/2003 |
| WO | WO 03/054045 | 7/2003 |
| WO | WO 2004/100664 | 11/2004 |
| WO | WO 2004/103071 | 12/2004 |
| WO | WO 2005/061022 | 7/2005 |
| WO | WO 2005/107455 | 11/2005 |
| WO | WO 2007/058880 | 5/2007 |
| WO | WO 2007/070649 | 6/2007 |
| WO | WO 2007/070650 | 6/2007 |
| WO | WO 2007/100653 | 9/2007 |
| WO | WO 2008/157323 | 12/2008 |

OTHER PUBLICATIONS

Richards, E.G., *An Introduction to Physical Properties of Large Molecules in Solution*, IUPAB Biophysics Series, Cambridge University Press, Cambridge, (1980), 6 pages.

Barton, A.F.M. *Handbook of Solubility and Other Cohesion Parameters*, 2nd Ed. CRC Press, Boca Raton, FL, (1991), 6 pages.

*Polymer Handbook, 3rd Ed.*, J. Brandrup & E.H. lmmergut, Eds. John Wiley, NY pp. 519-557 (1989).

Barton, A.F.M., *Handbook of Polymer-Liquid interaction Parameters and Solubility Parameters*, CRC Press, Boca Raton, FL, (1990), 5 pages.

ASTM E2180-01; Standard Test Method for Determining the Activity of Incorporated Antimicrobial Agent(s) in Polymeric or Hydrophobic Materials, 2004, 3 pages.

Decker, C.; The Use of UV Irradiation in Polymerization. Polymer International 1998, 45, 133-141.

URL <http://www.merriam-webster.com/dictionary/matrix>, [printed from the internet on Mar. 15, 2011], 2 pgs.

URL <http://www.britannica.com/EBchecked/topic/369081/materials-science/32304/Thermoplastic>, [printed from the internet on Mar. 15, 2011], 2 pgs.

* cited by examiner

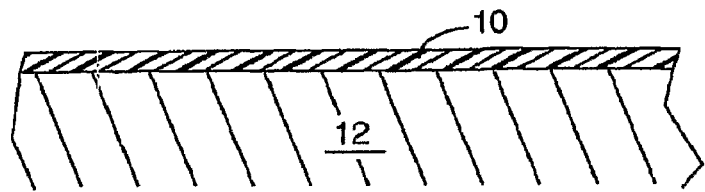
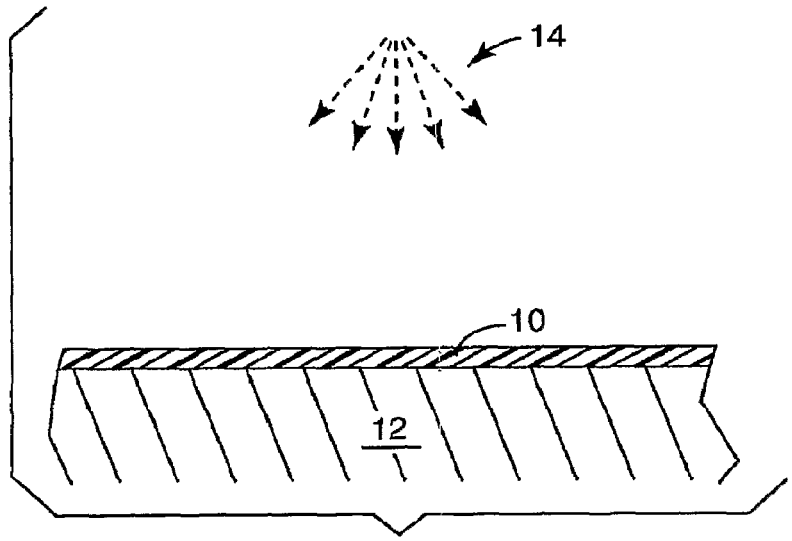
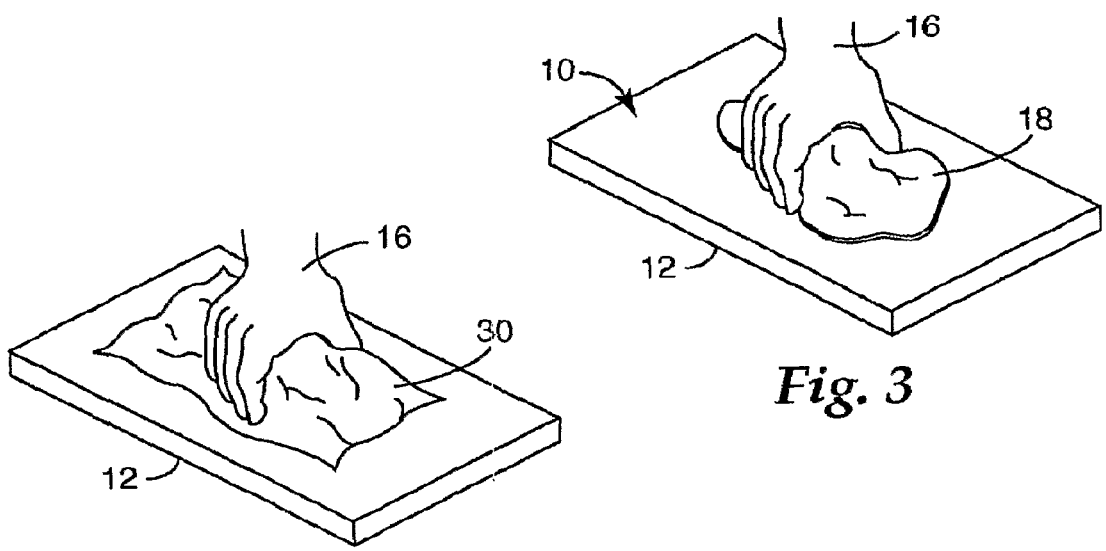

ANTIMICROBIAL COATING SYSTEM

CROSS-REFERENCE TO RELATED APPLICATION(S)

Priority is claimed under 35 U.S.C. 371 to PCT Application No. PCT/US2006/047779, filed Dec. 14, 2006, which claims priority to U.S. Provisional Patent Application No. 60/743, 037, filed Dec. 14, 2005, and U.S. Provisional Patent Application No. 60/743,038, filed Dec. 14, 2005, the disclosures of which are incorporated herein by reference in their entirety.

FIELD OF THE INVENTION

The present invention relates to antimicrobial coatings. In particular, the present invention relates to removable antimicrobial coatings for use on surfaces to reduce the risk of contamination by microorganisms.

BACKGROUND

Contamination by microorganisms can have dramatic impact on human life and health. During everyday routines, people continuously come into contact with a variety of surfaces that are contaminated with one or more types of microorganisms, some of which may be pathogens. Such surfaces may include countertops, tables, and food preparation surfaces in restaurants, splash guards and conveyor belts in food processing plants, public facilities, display applications, and a variety of surfaces in healthcare settings. Contamination with pathogenic microorganisms in such locations may result in the spread of disease and infections to people, which correspondingly endangers human lives and increases health care costs.

To counter the spread of undesired microorganisms, frequently touched, potentially contaminated surfaces are typically cleaned and sanitized on a regular basis. While this provides an immediate reduction in concentration of microorganisms on given surfaces, the surfaces must be repeatedly cleaned and sanitized on a frequent basis to continue to prevent contamination by microorganisms. One reason for this is because many antimicrobial materials used for cleaning and sanitation become deactivated when the surface is dried. In addition, many articles used to wipe visible dirt from surfaces may recontaminate the wiped surface with microorganisms that will grow and cause a cross-contamination hazard. For example, tables and food preparation surfaces at restaurants are continuously wiped with a sponge or towel to remove excess consumables and garbage. The article used for wiping frequently harbors pathogenic microorganisms that are transferred to the wiped surface.

SUMMARY

Some aspects of the present invention provide an antimicrobial coating system. The antimicrobial coating system can include a film-forming composition comprising a polymer having an effective molecular weight, and an effective amount of an antimicrobial agent dispersed within the polymer. The film-forming composition can form a water-insoluble, biocidal antimicrobial film when applied to a surface.

In some aspects of the present invention, a film-forming composition is provided. The film-forming composition can include a polymer and an effective amount of an antimicrobial agent dispersed within the polymer. The polymer can include at least one of acrylic, urethane, polyvinyl alcohol having an effective molecular weight, and combinations thereof. The antimicrobial agent can include at least one of a fatty acid monoester, a fatty acid monoether, a transition metal ion-containing compound, a quaternary ammonium-containing compound, a biguanide, and combinations thereof.

Some aspects of the present invention provide an antimicrobial film comprising a polymer having an effective molecular weight, and an effective amount of an antimicrobial agent. The antimicrobial film can be water-insoluble and biocidal.

BRIEF DESCRIPTION OF THE DRAWINGS

FIG. 1 is a side sectional view of an antimicrobial film of the present invention disposed on a surface.

FIG. 2 is a side sectional view of the antimicrobial film disposed on the surface, with a remover composition of the present invention being deposited on the antimicrobial film.

FIG. 3 is a top perspective view of a hand of a user removing the antimicrobial film from the surface with a wipe article.

FIG. 4 is a top perspective view of an article in use for applying an antimicrobial coating system of the present invention to a surface to form an antimicrobial film of the present invention.

While the above-identified drawings set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

FIG. 1 is a side sectional view of antimicrobial film 10 disposed on surface 12, where antimicrobial film 10 is formed by a film-forming composition that can form a first part of a two-part antimicrobial coating system of the present invention. As discussed below, the second part of the antimicrobial coating system is a remover composition (not shown in FIG. 1) that includes a solvent suitable for removing antimicrobial film 10 from surface 12.

Surface 12 may be any surface that may incur contamination by microorganisms, such as table and counter tops, food preparation surfaces, surfaces found in publicly used locations and facilities (e.g., public telephones, public transportation, and public lavatory facilities), touch-screen displays, door handles, light switches, and surfaces found in healthcare settings (e.g., bed rails and side tables). While surface 12 is shown as a flat, planar surface, antimicrobial film 10 may also be coated on curved and irregular shaped surfaces. As used herein and in the appended claims, the term "microorganism," "microbe," or a derivative thereof, is used to refer to any microscopic organism, including without limitation, one or more of bacteria, viruses, algae, fungi and protozoa. In some cases, the microorganisms of particular interest are those that are pathogenic, and the term "pathogen" is used herein to refer to any pathogenic microorganism.

As described above, antimicrobial film 10 is derived from a film-forming composition that is coated onto surface 12, where the film-forming composition includes a polymer of an effective molecular weight to provide a water-insoluble antimicrobial film 10 and an effective amount of one or more antimicrobial agents to reduce microorganism contamination. In some embodiments, the antimicrobial agents are dispersed within the polymer in a releasable manner, which allows the antimicrobial agents to be released from antimicrobial film 10 at an effective diffusion rate to reduce microorganism contamination on surface 12. In some embodiments, reducing microorganism contamination includes providing biocidal activity. As used herein and in the appended claims, the term "biocidal" is used to describe an antimicrobial film 10 that kills microorganisms that come into contact with the antimicrobial film 10. As a result, biocidal activity is distinguishable over systems that merely provide inhibition of microorganism growth, because a film that inhibits growth and/or reproduction of microorganisms does not necessarily kill the microorganisms. In some embodiments, as further taught by the examples, biocidal activity, and particularly, extended biocidal activity (e.g., after 24 hours) can be demonstrated by the microbial load reductions exhibited by the antimicrobial film 11, when tested pursuant to ASTM E2180-01.

While disposed on surface 12, antimicrobial film 10 is resistant to removal by moderate frictional forces, such as frictional forces applied when a user uses a wipe article (e.g., a cloth towel or sponge) to wipe food or waste from surface 12. This allows antimicrobial film 10 to provide antimicrobial protection to surface 12 without the risk of accidentally being removed while surface 12 is wiped clean. In some embodiments, antimicrobial film 10 is water-insoluble.

As used herein and in the appended claims, the term "water-insoluble" is used to refer to an antimicrobial film that does not dissolve (i.e., form a homogeneous solution) after 30 minutes of being placed in DI water at room temperature with no stirring. One example of a method for testing water-insolubility is by forming the antimicrobial film onto a release liner, peeling the antimicrobial film from the release liner and submerging the antimicrobial film in DI water at room temperature for 30 minutes with no stirring. If, after 30 minutes, in these conditions, at least a portion of the antimicrobial film still remains intact and has not gone into solution, the antimicrobial film is "water-insoluble." As a result, if an antimicrobial film swells in water under these conditions, but does not dissolve to form a homogeneous solution, the antimicrobial film is "water-insoluble."

When desired, antimicrobial film 10 may be removed from surface 12 with a remover composition, and a fresh coating of antimicrobial film 10 may be applied to provide continuing antimicrobial protection to surface 12. When removal of antimicrobial film 10 is desired, the remover composition may be applied, and antimicrobial film 10 may then be wiped off from surface 12 under moderate frictional forces. As a result, the antimicrobial coating system of the present invention is a convenient system for applying and removing durable antimicrobial coatings having biocidal activity to and from a variety of surfaces.

Suitable polymers for use in the film-forming composition of antimicrobial film 10 include water-soluble polymers, organic solvent-soluble polymers, and water-based polymer dispersions. Examples of water-soluble polymers include polyvinyl alcohols, polyvinylpyrrolidones, polyethylene oxides, sulfonated polyurethanes, copolymers thereof, and combinations thereof. Suitable commercially available polyvinyl alcohols include those available from J. T. Baker, Phillipsburg, N.J., and from Sigma-Aldrich Company, St. Louis, Mo. Suitable commercially available polyvinylpyrrolidones include those available from J. T. Baker, and those available under the trade designations "PVP-Kxx" from Peakchem, ZheJiang, China, where the "xx" number after the letter K indicates the average molecular weight (in 1,000 s of Daltons) of the polymer (e.g., "PVP-K90" and "PVP-K30").

Suitable commercially available polyethylene oxide polymers include those available under the trade designation "POLYOX" from Dow Chemical Co., Midland, Mich. Suitable water-soluble polymers may have a wide range of molecular weights, where the molecular weight generally determines the product performance. For example, if the polymer molecular weight is too low, the film coating may be tacky and easily removable (i.e., has poor durability and is water-soluble). Alternatively, if the molecular weight of the polymer is too high, the coating solution exhibits poor solubility, which results in the film being difficult to remove. For applications in which the antimicrobial film 10 will need to be removed and replenished from time to time, suitable molecular weights provide good film durability, water-insolubility, and relative ease of removal by an appropriate remover composition. That is, in some embodiments, an effective molecular weight refers to a molecular weight that allows the resulting antimicrobial film 10 to be water-insoluble. For example, in some embodiments, an effective molecular weight of polyvinyl alcohol is at least about 100,000 Daltons, particularly, at least about 120,000, and more particularly, at least about 150,000 Daltons.

Suitable organic solvent-soluble polymers include polyurethanes, acrylic polymers, polyamides, copolymers thereof, and combinations thereof. Commercially available solvent-based polyurethanes include those available under the trade designation "PERMUTHANE" from Stahl USA, Peabody, Mass. (e.g., "SU26-248", which is an aliphatic polyurethane in toluene). Other suitable polyurethanes include those commercially available under the trade designations "ESTANE" from B.F. Goodrich, Cleveland, Ohio (e.g., "Estane 5715" and "Estane 5778"), and "MORTHANE" from Huntsman Polyurethanes, Ringwood, Ill. (e.g., "CA118" and "CA237" polyester polyurethanes). Additional suitable polymers include those commercially available under the trade designation "U-371" from DSM NeoResins, Wilmington, Mass.

Examples of water-based polymer dispersions include polyurethanes, polyureas, polyacrylics, polyethers, polyester, and copolymers thereof and combinations thereof. Suitable aqueous dispersions include urethanes such as those commercially available under the trade designation "NEOREZ" from DSM NeoResins, Wilmington, Mass. (e.g., "NEOREZ R-960" and "NEOREZ R-9699"); acrylics such as those commercially available under the trade designation "NEOCRYL" from DSM NeoResins (e.g., "NEOCRYL XK-90", "NEOCRYL XK-96", and "NEOCRYL XK-95"); and acrylic urethane copolymers such as those commercially available under the trade designation "NEOPAC" from DSM NeoResins, Additional suitable water-based urethanes include those commercially available under the trade designations "RU-077" and "RU-075" from Stahl USA, Peabody, Mass.

Water-soluble materials can be suitable for use in situations where antimicrobial film 10 remains dry until the intended removal with a water-based remover composition. The above-listed materials may also be partially or fully cross-linked to improve the mechanical structure of the polymer, and to reduce the water solubility of such materials. Polymers having reduced water solubility are beneficial for use on surfaces (e.g., surface 12) that come into contact with water (e.g., surfaces that are rinsed or soaked with water). To initiate the cross-linking, the polymer may include curing agents, such as chain extension agents, chemical cross-linking agents, and radiation cross-linking agents (e.g., photoinitiators).

To initiate the cross-linking, the film-forming composition may include cross-linking agents, such as chain extension agents and chemical cross-linking agents. Examples of cross-linking agents include isocyanates such as those commercially available under the trade designation "DESMODUR" from Bayer AG, Pittsburg, Pa.; aziridine crosslinkers such as those commercially available under the trade designation "CX-100" from DSM NeoResins, Wilmington, Mass.; and those commercially available under the trade designation "XR-2500)" from Stahl USA, Peabody, Mass. Suitable chain extension agents include carbodiimides such as those commercially available under the trade designation "EX62-944", and melamines such as those commercially available under the trade designation "XR-9174", both from Stahl USA.

Examples of particularly suitable cross-linkable polymer compositions include self cross-linking polymer dispersions, where the deposited coating self cross-links upon drying to form a durable, water-insoluble coating layer. Self cross-linking polymer dispersions typically contain side groups that react to form chemical bonds via condensation polymerizations, which take place upon evaporation of water. Self cross-linking polymer dispersions offer the advantage of forming antimicrobial films (e.g., antimicrobial film 10) that are solvent resistant without requiring cross-linking agents. Various types of cross-linking agents can pose potential health risks because they are small, solvent-borne, organic molecules (e.g., isocyanates).

Examples of self cross-linking urethane dispersions include polyester-urethanes that are terminated by hydrolysable silyl groups and contain solubilizing sulfonic acid functional groups. Such polyester-urethanes are described in Krepski, et al., U.S. Pat. No. 5,929,160, which is incorporated by reference in its entirety. Additional examples of suitable self cross-linking urethane dispersions include polyurethane water-based dispersions containing hydroxyl groups to accomplish the self cross-linking function. Suitable hydroxyl group-based polyurethanes include those prepared pursuant to the process described in Mazanek et al., U.S. Pat. No. 7,049,367, which is incorporated by reference in its entirety. Even further additional examples of suitable self cross-linking urethane dispersions include polyurethane polymer hybrid dispersions based on oxidatively drying polyols, such as those disclosed in Ingrisch et al., U.S. Pat. No. 6,462,127, which is incorporated by reference in its entirety.

Examples of commercially available self cross-linking polymers include dispersions sold under the trade designations "RHEOPLEX" and "ROVACE" available from Rohm and Haas Company, Philadelphia, Pa., which are typically used as binders for textile and non-woven substrates for the protection of color dyes applied to the substrates. Exemplary compositions include the trade designated "RHEOPLEX HA-12" (non-ionic dispersion with glass transition temperature of about 19° C.) and "RHEOPLEX TR-407" (anionic dispersion with glass transition temperature of 34° C.), both of which exhibit good wash durability and chemical resistance. Additional examples of commercially available self cross-linking polymers include the trade designated "NEOREZ R-551" polyether-based polymers and "NEOCRYL XK-98" acrylic emulsion polymers, both of which are available from DSM NeoResins, Wilmington, Mass. The "NEOCRYL XK-98" acrylic emulsion polymers are particularly suitable because they provide good adhesion to most substrates and exhibit high gloss and block resistance.

Suitable concentrations of the polymer in the film-forming composition of antimicrobial film 10, after application and drying of the film, include any concentration that is effective for dispersing and containing the antimicrobial agents. Examples of suitable concentrations of the polymer in the film-forming composition of antimicrobial film 10 range from about 50% by weight to about 99.9% by weight, with particularly suitable concentrations ranging from about 70% by weight to about 99% by weight, and with even more particularly suitable concentrations ranging from about 90% by weight to about 95% by weight.

Suitable antimicrobial agents for use in the film-forming composition of antimicrobial film 10 include any inorganic or organic antimicrobial agent that is effective for reducing microbial contamination. Examples of suitable antimicrobial agents include transition metal ion-containing compounds, (e.g., silver, zinc, copper, gold, tin and platinum-based compounds), fatty acid monoesters/monoethers, triclosan, peroxides, iodines, quaternary ammonium-containing compounds, biguanides, complexes thereof (e.g., iodophores), derivatives thereof, and combinations thereof.

Examples of suitable silver-containing compounds include silver sulfate, silver acetate, silver chloride, silver lactate, silver phosphate, silver stearate, silver thiocyanate, silver proteinate, silver carbonate, silver nitrate, silver sulfadiazine, silver alginate, silver nanoparticles, silver-substituted ceramic zeolites, silver complexed with calcium phosphates, silver-copper complexed with calcium phosphates, silver dihydrogen citrates, silver iodines, silver oxides, silver zirconium phosphates, silver-substituted glass, and combinations thereof.

Suitable commercially available silver zeolite-containing compounds include those sold under the trade designation "AGION" from AgION Technologies Inc., Wakefield, Mass.; those available under the trade designations "IRGAGUARD B5000" and "IRGAGUARD B8000", which are based on AgZn zeolites supplied by Ciba Specialty Chemicals, Tarrytown, N.Y.; as well as those available under the trade designation "ALPHASAN", which are silver sodium hydrogen zirconium phosphates, supplied by Milliken Chemicals, Spartanburg, S.C. Suitable commercially available silver chloride-containing compounds include those available under the trade designation "JMAC" from Clariant Corporation, Charlotte, N.C.

Examples of suitable commercially available organic antimicrobial agents include polymeric quaternary ammonium salts such as 2-butenyldimethyl ammonium chloride polymers commercially available under the trade designation "POLYQUAT" from Arch Chemicals, Inc., Norwalk, Conn.; phenolic compounds such as phenol and its derivatives, parabens, and triclosan, which has the chemical formula 2,4,4'-trichloro-2'-hydroxy diphenyl ether, and is commercially available from Ciba Specialty Chemicals, Tarrytown, N.Y.; poly (iminoimidocarbonylimidocarbonyliminohexamethylene hydrochlorides), commercially available under the trade designation "VANTOCIL P" from Arch Chemicals, Inc., Norwalk, Conn.; polyhexamethylene biguanides, antimicrobial lipids such as those disclosed in Scholz et al., U.S. Publication No. 2005/0089539, which is incorporated herein by reference, antimicrobial acids (e.g., fatty acids, benzoic acids, and salicylic acids), antimicrobial natural oils (e.g., tea tree oils, and grape fruit seed extracts), and combinations thereof. Additional suitable organic antimicrobial agents include organic salts of transition metals (i.e., organometallic antimicrobial agents), such as silver salts (e.g., silver lactate), copper salts (e.g., copper napthenate), zinc salts, and tin salts (e.g., trialkyl tin hydroxides and triaryl tin hydroxides).

Suitable antimicrobial lipids include, for example, fatty acid monoesters/monoethers. In some embodiments, the fatty acid monoesters/monoethers suitable for the antimicrobial agent are considered food grade and recognized as safe (GRAS) by the U.S. Food and Drug Administration (FDA). Such fatty acid monoesters/monoethers may be derived from C8 to C12 fatty acids such as glycerol monoesters of caprylic acid, capric acid, and lauric acid; propylene glycol monoesters of caprylic acid, capric acid, and lauric acid; and combinations thereof. Examples of suitable fatty acid monoesters include, but are not limited to, glycerol monolaurate commercially available under the trade designation "LAURICIDIN" from Med-Chem Laboratories, East Lansing, Mich.; glycerol monocaprylate commercially available under the trade designation "POEM M-100" from Riken Vitamin Ltd., Tokyo, Japan; glycerol monocaprate commercially available under the trade designation "POEM M-200" from Riken Vitamin Ltd.; propylene glycol monolaurate propylene glycol monocaprylate, and propylene glycol monocaprate, all commercially available from Uniquema International, Chicago, Ill.; and combinations thereof.

Examples of suitable concentrations of the fatty acid monoesters/monoethers range from about 1.0% to about 30.0% by weight. Examples of particularly suitable concentrations of the fatty acid monoesters/monoethers in the composition range from about 5.0% to about 20.0% by weight.

The antimicrobial agent may also include an enhancer and/or a surfactant for use with the fatty acid monoesters/monethers, as discussed in Andrew et al., PCT application No. WO 00/71183, entitled "Antimicrobial Articles," and in Andrews et al., PCT Application No. WO01/43549, entitled "Fruit, Vegetable, and Seed Disinfectants," both of which are incorporated herein by reference in their entireties.

Suitable concentrations of the antimicrobial agents in the film-forming composition of antimicrobial film 10 include any concentration that is effective for providing biocidal activity. This may vary depending on the type of antimicrobial agent used. Examples of suitable concentrations of the antimicrobial agents in the film-forming composition of antimicrobial film 10 range from about 0.1% by weight to about 20% by weight, with particularly suitable concentrations ranging from about 1% by weight to about 10% by weight.

In some embodiments, the antimicrobial agent may at least partially interact with the polymer (i.e., form non-covalent bonds (e.g., ionic bonds, hydrogen bonds, matrix interactions, etc.) or covalent bonds with the polymer) so as not to be sufficiently available to provide biocidal activity to microorganisms that come into contact with the antimicrobial film 10. In other words, the resulting antimicrobial film may not have a sufficient surface concentration of the antimicrobial agent to provide biocidal activity. In such embodiments, a higher concentration of antimicrobial agent may be needed to provide biocidal activity. As a result, in some embodiments, an effective amount of antimicrobial agent is an amount that provides biocidal activity to microorganisms that come into contact with the antimicrobial film 10.

A "sufficiently available" antimicrobial agent or a "sufficient surface concentration" of the antimicrobial agent in the antimicrobial film 10 is sometimes used to refer to an antimicrobial film having microbial load reductions of at least 90% against gram positive or gram negative pathogens when tested pursuant to ASTM E2180-01, particularly, microbial load reductions of at least 90% against gram positive and gram negative pathogens when tested pursuant to ASTM E2180-01, particularly, microbial load reductions of at least 99% against gram positive or gram negative pathogens when tested pursuant to ASTM E2180-01, and more particularly, microbial load reductions of at least 99% against gram positive and gram negative pathogens when tested pursuant to ASTM E2180-01.

The film-forming composition may also include fast-acting antimicrobial agents that may not provide antimicrobial activity over extended periods of time, but which provide fast antimicrobial activity of a relatively short duration upon application of the film-forming composition to surface 12. Examples of suitable fast-acting antimicrobial agents include quaternary ammonium salts, benzalkonium chlorides, biguanide compounds (e.g., halogenated hexidines such as chlorhexidine, chlorhexidine gluconate, and chlorhexidine acetate), alcohols (e.g., low molecular weight alcohols such as ethyl alcohol and isopropyl alcohol), bleach, hydrogen peroxide, urea hydrogen peroxide, hydrogen peroxide stabilized in a sodium pyrophosphate matrix, hydrogen peroxide chelated in polyvinylpyrrolidone, and combinations thereof. Examples of suitable commercially available quaternary ammonium salts include didecyl dimethyl ammonium chlorides available under the trade designation "BTC 1010" from Stepan Company, Northfield, Ill., and under the trade designation "BARDAC 2250" from Lonza Group Ltd., Valais, Switzerland; dialkyl dimethyl ammonium chlorides available under the trade designation "BARDAC 2050 also from Lonza Group Ltd.; and alkyl dimethyl benzyl ammonium chloride available under the trade designation "BARQUAT MB-50" also from Lonza Group Ltd.

Suitable concentrations of the fast-acting antimicrobial agents in the film-forming composition of antimicrobial film 10 include any concentration that is effective for reducing microbial contamination, and may depend on the type of fast-acting antimicrobial agent used. For example, when the fast-acting antimicrobial agent is an alcohol, suitable concentrations of the alcohol in the film-forming composition range from about 20% by weight to about 80% by weight, with particularly suitable concentrations ranging from about 40% by weight to about 60% by weight. Examples of suitable concentrations of the antimicrobial agents in the film-forming composition of antimicrobial film 10 when quaternary amines are used range from about 0.001% by weight to about 10% by weight, with particularly suitable concentrations ranging from about 0.1% by weight to about 5% by weight.

The film-forming composition may also include surfactants and thickeners to modify wetting and flow properties. Examples of suitable surfactants include the trade designated "SURFONIC L" series surfactants commercially available from Huntsman Corporation, Salt Lake City, Utah; and the trade designated "ZONYL" surfactants commercially available from E. I. du Pont de Nemours and Company. Examples of suitable thickeners include starch, gum arabic, guar gum, and carboxymethylcellulose. A particularly suitable thickening agent is commercially available under the trade designation "NEOCRYL-A1127" from DSM NeoResins, Wilmington, Mass. Examples of suitable total concentrations of surfactants and thickeners in the film-forming composition of antimicrobial film 10 range from about 1% by weight to about 20% by weight, with particularly suitable total concentrations ranging from about 5% by weight to about 10% by weight.

Additional optional components that may be incorporated into the film-forming composition include buffering agents and pH adjusting agents, fragrances or perfumes, dyes and/or colorants, solubilizing materials, defoamers, lotions and/or mineral oils, essential oils, enzymes, bleaching agents, preservatives, indicator dyes, and combinations thereof. Examples of suitable total concentrations of the optional components in the film-forming composition of antimicrobial film 10 range from about 1% by weight to about 20% by weight, with particularly suitable total concentrations ranging from about 1% by weight to about 5% by weight. The film-forming composition of antimicrobial film 10 may contain a dye to allow color tinting of antimicrobial film 10 if desired.

Tinted films allow the end user to visually verify the film coverage of surface 12 and, after applying the remover composition, visually ensure that all of antimicrobial film 10 has been removed from surface 12. Furthermore, indicator dyes provide color to the formulation allowing a user to visually verify the film coverage of surface 12, but the color disappears upon drying (e.g., upon exposure to air) within a short time period (e.g., few seconds or minutes) leaving a colorless film. Examples of suitable indicator dyes include dyes based on phthalein chemistry, such as phenolphthalein (pink), thymolphthalein (blue), and o-cresolphthalein (purple), all of which are obtainable from Sigma-Aldrich Chemical Company, Saint Louis, Mo. Such indicator dyes also allow a user to check that antimicrobial film 10 is still intact by wetting the surface 12. For example, in some embodiments, if antimicrobial film 10 including the indicator dye is still intact on the surface 12, the surface 12 will change color upon wetting (e.g., with water, a high pH solution (such as WINDEX-brand glass cleaner solution), an ammonia solution, or whatever substance to which the indicator dye is sensitive). This would indicate to the user, for example, that antimicrobial film 10 is still applied to the surface 12.

The film-forming composition of antimicrobial film 10 may be formed by blending the antimicrobial agent, the polymer, and any optional components together. This may be performed as a solution in a solvent, where the solvent is selected to substantially dissolve or disperse the antimicrobial agent, the polymer, and any optional components. Examples of suitable solid concentrations in the solvent for the resulting film-forming composition range from about 5% by weight to about 50% by weight. For water-based polymer dispersions, higher concentrations of solids may be achieved without an increase in the solution viscosity. Accordingly, particularly suitable solid concentrations in the solvent for water-based polymer dispersions range from about 10% to about 40% by weight. For non-dispersion water-based coatings, and for solvent-based coatings, particularly suitable solid concentrations in the solvent range from about 5% to about 20% by weight.

The film-forming composition may then be applied to surface 12 and dried to form antimicrobial film 10. The film-forming composition may be applied to surface 12 in a variety of manners, such as by spraying, brushing, rod coating, or by wiping the film-forming composition onto surface 12 with a wipe article.

For example, FIG. 4 is a top perspective view of an article 30 being wiped across surface 12 by hand 16 of a user. Article 30 is a wipe article that includes a substrate and a film-forming composition impregnated within the substrate. As the user wipes article 30 across surface 12, the film-forming composition is extracted from the substrate of article 30 and deposits on surface 12. This forms a thin, continuous antimicrobial film 10 on surface 12.

The substrate of article 30 may be any type of woven, non-woven, knitted, foam, or sponge substrate, or combinations thereof, that is capable of being impregnated with the film-forming composition. The substrate may consist of a single layer or multiple layers of one or more materials. Non-woven substrates are particularly suitable because of their utility in the manufacture of cleaning and scouring articles.

Because the film-forming composition is extracted from the substrate during use, article 30 is particularly suitable as a disposable wipe (i.e., article 30 may be formed from substrate materials intended to be discarded after use). Examples of suitable disposable wipe materials for the substrate of article 30 include spun-bond and spun-lace non-woven materials having a basis weight ranging from about 15 grams/meter$^2$ to about 75 grams/meter$^2$. Such materials are generally made of synthetic polymers, natural polymers, and combinations thereof. Suitable synthetic polymers include rayon polyester, polyethylene terephthalate (PET), polyvinyl chloride, polyacrylamide, polystyrene, polyethersulfone, acrylics and acrylic copolymers, rayon, polyolefins (e.g., polypropylene), and combinations thereof. Suitable natural polymers include wood pulp, cotton, cellulose, rayon, and combinations thereof.

In alternative embodiments, article 30 may be formed from materials used for semi-disposable or reusable wipes. Examples of suitable semi-disposable wipe materials for the substrate of article 30 include spun-lace non-woven materials having a basis weight ranging from about 75 grams/meter$^2$ to about 250 grams/meter$^2$. Such materials may be formed from fibers or microfibers of polyester, polyamide, viscose, or combinations thereof. Examples of suitable reusable wipe materials for the substrate of article 30 include knitted, woven, thermo-bonded, latex-coated, and chamois-type materials having a basis weight ranging from about 100 grams/meter$^2$ to about 300 grams/meter$^2$. Such materials may be formed from fibers or microfibers of polyester, rayon, viscose, polypropylene, natural fibers, polyamides, or combinations thereof.

Examples of suitable commercially available wipe materials include those sold under the trade designation "SONTARA", non-woven fabrics available from Du Pont such as SONTARA 8001 (100% polyester substrate) and SONTARA 8100 (50% polyester/50% Dacron). Other suitable wipe materials include those designated as M001, M022, and M017, and are 100% spunlaced polyester materials available from Polymer Group Inc., Wilmington, Del. Other polyester substrate materials can be obtained from Jacob Holms Industries under the designation 350160 and 10203-003.

In some embodiments, article 30 is glove-shaped to receive hand 16 of the user. This provides a convenient means for the user to wipe article 30 across surface 12 to extract the film-forming composition. In some embodiments, the glove-shaped article 30 includes a barrier layer (e.g., a flexible polymeric layer) between the substrate containing the film-forming composition and the hand 16 of the user. This can inhibit contact between the film-forming composition and hand 16 of the user, thereby reducing the risk of irritating the skin of hand 16.

The film-forming composition that is impregnated within the substrate includes a polymer, one or more antimicrobial agents, and a solvent. In some embodiments, the polymer and the antimicrobial agent are substantially dissolved in the solvent, and the solvent is impregnated within the substrate, thereby retaining the polymer and the antimicrobial agents (and any optional components) within the substrate. Examples of suitable concentrations of the film-forming composition in article 10, prior to extraction, range from about 50% by weight to about 500% by weight of the substrate, based on a dry weight of the substrate. Examples of particularly suitable concentrations of the film-forming composition in article 10, prior to extraction, range from about 100% by weight to about 400% by weight of the substrate, based on a dry weight of the substrate.

The film-forming composition may be impregnated within the substrate in a variety of manners, such as spraying, knife coating, roll coating, curtain coating, spin coating, immersion coating, and combinations thereof. After impregnation and prior to use, the substrate is at least partially saturated with the film-forming composition. The resulting article 10 may then be packaged in a sealed environment (individually or with multiple articles) to prevent the solvent from evaporating. When the user desires to apply an antimicrobial film on surface 12, the user may wipe article 10 across surface 12 while applying a moderate amount of pressure. The applied pressure and the frictional force imposed by the wiping action causes portions of the film-forming composition to deposit from the substrate of article 10. In particular, the polymer, the antimicrobial agent, and the solvent of the film-forming composition are each deposited from the substrate of article 10. This is in contrast to conventional antimicrobial wipes, in which only an antimicrobial (and typically a solvent) are deposited. By depositing the polymer with the antimicrobial agent and the solvent, the resulting antimicrobial film coated on surface 12 prevents the antimicrobial agent from being immediately washed away when surface 12 is cleaned.

The amount of film-forming composition extracted is dependent on the pressure applied, the extent of the wiping action, and the concentration of the film-forming composition impregnated within the substrate. In some embodiments, the amount of film-forming composition extracted is enough to form a dried antimicrobial film having a layer thickness on surface 12 (after drying) ranging from about 1 micrometers to about 100 micrometers, and particularly, ranging from about 2 micrometers to about 50 micrometers. This can provide a suitable concentration of antimicrobial agents to reduce the risk of microorganism contamination.

After use, article 30 may be discarded. Alternatively, if article 30 retains a useable portion of the impregnated film-forming composition, article 30 may be reused to apply antimicrobial films to additional surfaces until the reservoir of film-forming composition impregnated within substrate 12 is depleted. Accordingly, article 30 may be used as a disposable or semi-disposable wipe article by consumers. However, article 30 may also be re-impregnated with an additional supply of the film-forming composition for subsequent use. This increases the product life of article 30.

After being applied to surface 12, the film-forming composition may be dried to remove the solvent. Suitable drying techniques include air drying (e.g., forced or passive) at room temperature or elevated temperatures. The use of volatile solvents (e.g., isopropanol and acetone) can be useful for increasing the rate of drying. After drying, the resulting antimicrobial film is a thin, continuous film that provides antimicrobial protection to surface 12, as discussed above. In some embodiments, the polymer matrix may also be fully or partially cross-linked after being applied to surface 12 and dried. This can increase the mechanical integrity of the antimicrobial film, thereby allowing the antimicrobial film to provide abrasion and chemical resistance to surface 12 in addition to antimicrobial activity.

Examples of suitable layer thicknesses for antimicrobial film 10 (after drying) range from about 1 micrometer to about 500 micrometers, with particularly suitable layer thicknesses ranging from about 2 micrometers to about 50 micrometers. Once applied, antimicrobial film 10 is a thin, durable film that provides antimicrobial protection to surface 12, as discussed above. In some embodiments, antimicrobial film 10 is also a transparent film, which allows the aesthetic qualities of the underlying surface (e.g., surface 12) to be visually observed through antimicrobial film 10.

As discussed above, after application to surface 12, antimicrobial film 10 exhibits antimicrobial activity to reduce the microorganism contamination of surface 12, and particularly, exhibits biocidal activity. Examples of suitable levels of biocidal activity include microbial load reductions of at least about 90% for at least one of *S. aureus* (gram positive) and *Ps. aeruginosa* (gram negative) pathogens. Examples of even more suitable levels of biocidal activity include microbial load reductions of at least about 99% for at least one of *S. aureus* (gram positive) and *Ps. aeruginosa* (gram negative) pathogens. Examples of particularly suitable levels of biocidal activity include microbial load reductions of at least about 90% for both of *S. aureus* (gram positive) and *Ps. aeruginosa* (gram negative) pathogens. Finally, examples of even more particularly suitable levels of biocidal activity include microbial load reductions of at least about 99% for both of *S. aureus* (gram positive) and *Ps. aeruginosa* (gram negative) pathogens. The "microbial load reductions" herein refer to microbial load reductions obtained pursuant to ASTM E2180-01.

Antimicrobial film 10 may also include an end-of-service indicator to provide visual indication prompting the user to replace antimicrobial film 10. Examples of suitable end-of-service indicators include time-temperature indicators and color changing dyes. An end-of-service indicator may be applied to antimicrobial film 10 in the form of a label or paint to the corners of antimicrobial film 10 after antimicrobial film 10 is formed on surface 12. In some embodiments, the indicator is calibrated to indicate a color change at about the time when the corresponding antimicrobial layer 10 should be replaced (e.g., when the antimicrobial activity levels have substantially decreased or are exhausted).

Time-temperature indicators typically operate by chemical reaction mechanisms, diffusion mechanisms, and capillary driven, fluid-wicking mechanisms. Examples of suitable time-temperature indicators are disclosed in Bommarito, et al., U.S. Pat. No. 6,741,523 (i.e., microstructured time-dependent indicators) and Arens, et al., U.S. Pat. No. 5,667,303, both of which are incorporated by reference in their entireties, and in *The Wiley Encyclopedia of Packaging Technology*, 400-406 (John Wiley & Sons, 1986) under the section entitled "Indicating Devices". Examples of suitable commercially available time-temperature indicators include those sold under the trade designations "MONITOR MARK" from 3M Corporation, St. Paul, Minn.; "WARM MARK" from Dry Pak Industries, Studio City, Calif.; "FRESH CHECK" from Lifelines Technology Inc., Morris Plains, N.J.; "VISTAB" from Visual Indicator Tag Systems AB, Malmb, Sweden; and "TT MONITOR" from Avery Dennison Corporation, Pasadena, Calif.

FIG. 2 is a side sectional view of antimicrobial film 10 disposed on surface 12, with remover composition 14 being deposited on antimicrobial film 10. Remover composition 14 is a solvent-based composition that dissolves and/or swells the film-forming composition of antimicrobial film 10, as discussed below. Remover composition 14 may be deposited on antimicrobial film 10 in a spray form as illustrated in FIG. 2. Alternatively, remover composition 14 may be incorporated in a wipe article that is wiped across antimicrobial film 10, thereby allowing remover composition 14 to dissolve and/or swell antimicrobial film 10 during the wiping process.

Remover composition 14 may include one or more solvents that are effective for dissolving the film-forming composition of antimicrobial film 10. Examples of suitable solvents for use in remover composition 14 include water, aqueous alkaline solvents, volatile solvents (e.g., acetone and isopropanol), glycols, and combinations thereof.

If the polymer in the film-forming composition of antimicrobial film 10 is not cross-linked, then the solvent of remover composition 14 may be selected to dissolve antimicrobial film 10. In some embodiments, the remover solvent is selected to closely match the solubility parameter of the polymer used. The term "solubility parameter" herein refers to the Hildebrand solubility parameter ($\delta$), which is a solubility parameter represented by the square root of the cohesive energy density of a material, having units of (pressure)$^{1/2}$, and being represented by the following equation:

$$\delta = \sqrt{\left(\frac{\Delta H - RT}{V}\right)} \quad (1)$$

where $\Delta H$ is the molar vaporization enthalpy of the material, R is the universal gas constant, T is the absolute temperature, and V is the molar volume of the solvent. Hildebrand solubility parameters are generally provided in conventional units of (calories/centimeter$^3$)$^{1/2}$((cal/cm$^3$)$^{1/2}$) and in SI units of megaPascals$^{1/2}$ (MPa$^{1/2}$).

Hildebrand solubility parameters are tabulated for solvents in Barton, A. F. M., *Handbook of Solubility and Other Cohesion Parameters*, 2$^{nd}$ Ed. CRC Press, Boca Raton, Fla., (1991), for monomers and representative polymers in Polymer Handbook, 3$^{rd}$ Ed., J. Brandrup & E. H. Immergut, Eds. John Wiley, NY pp. 519-557 (1989), and for many commercially available polymers in Barton, A. F. M., *Handbook of Polymer-Liquid Interaction Parameters and Solubility Parameters*, CRC Press, Boca Raton, Fla., (1990). Examples of suitable differences in Hildebrand solubility parameters between the polymer in the film-forming composition of antimicrobial film 10 and the solvent of remover composition 14 include differences of about 5.0 (cal/cm$^3$)$^{1/2}$, or less, with particularly suitable differences in Hildebrand solubility parameters including differences of about 2.0 (cal/cm$^3$)$^{1/2}$ or less, and with even more particularly suitable differences in Hildebrand solubility parameters including differences of about 1.0 (cal/cm$^3$)$^{1/2}$.

If the polymer in the film-forming composition of antimicrobial film 10 is cross-linked, then the solvent of remover composition 14 may be selected to either dissolve (by chemically disrupting and breaking the cross-links) antimicrobial film 10, swell (by absorbing into the cross-linked polymer matrix) antimicrobial film 10, or a combination thereof. Swelling takes place when the solvent of remover composition 14 penetrates into a cross-linked polymer network through the surface of antimicrobial film 10, which acts as a semi-permeable membrane. The solvent interacts with segments of the polymer network, which increases their mobility, disrupts the adhesion of the polymer segments to surface 12, and facilitates the removal of the film-forming composition. Swelling will take place only if the free energy of mixing between the solvent and the polymer segments is negative, where the free energy of mixing is defined as:

$$\Delta G_m = \Delta H_m - T\Delta S_m = RT(n_1 \ln \phi_1 + n_2 \ln \phi_2 + \chi_1 \phi_2 n_1) \quad (2)$$

where $\Delta G_m$ is the Gibbs free energy of mixing, $\Delta H_m$ is the enthalpy of mixing, T is the absolute temperature, $\Delta S_m$ is the entropy of mixing, R is the universal gas constant, $n_1$ is the molar fraction of the solvent in the swollen film, $\phi_1$ is the weight fraction of the solvent, $n_2$ is molar fraction of the polymer in the swollen film, $\phi_2$ the weight fraction of the polymer, and $\Omega_1$ is the Flory-Huggins interaction parameter. Equation (2) along with more detailed discussion of the theory of polymer swelling can be found in Richards, E. G., *An Introduction to Physical Properties of Large Molecules in Solution*, IUPAB Biophysics Series, Cambridge University Press, Cambridge, (1980).

Examples of suitable solvents for use in remover composition 14 when the polymer of the antimicrobial film is partially or fully cross-linked (i.e., polymers having reduced water solubility) include aqueous alkaline solvents (e.g., ammonia-containing solvents), volatile solvents (e.g., acetone and isopropanol), and combinations thereof. For example, when the film-forming composition of antimicrobial film 10 includes an alkali soluble acrylic copolymer dispersion commercially available under the trade designation "NEOCRYL BT-9" from DSM NeoResins, Wilmington, Mass., remover composition 14 may include a high pH solvent (e.g., an ammonia solution or soap-containing aqueous solvent) to dissolve and/or swell the antimicrobial film 10. Examples of suitable concentrations of the solvent in remover composition 14 range from about 50% by weight to 100% by weight, with particularly suitable total concentrations ranging from about 90% by weight to 100% by weight.

Remover composition 14 may also include surfactants and thickeners, and foaming agents to modify wetting and flow properties. Examples of suitable surfactants and thickeners include those discussed above for the film-forming composition of antimicrobial film 10. Examples of suitable total concentrations of surfactants and thickeners in remover composition 14 range from about 1% by weight to about 20% by weight, with particularly suitable total concentrations ranging from about 5% by weight to about 10% by weight.

FIG. 3 is a top perspective view of hand 16 of a user removing antimicrobial film 10 from surface 12 with wipe article 18. Prior to remover composition 14 being deposited, antimicrobial film 10 is resistant to being removed from surface 12, as discussed above. As such, antimicrobial film 10 must be subjected to at least a first minimum frictional force before being removed. The first minimum frictional force is greater than a moderate frictional force applied during a surface wiping with a wipe article. This prevents antimicrobial film 10 from being undesirably removed until remover composition 14 is deposited.

Remover composition 14, however, swells the polymer of the antimicrobial film 10 and/or breaks down the structural integrity of the polymer (i.e., dissolves the polymer), thereby allowing antimicrobial film 10 to be readily removed from surface 12. As a result, after remover composition 14 is deposited, antimicrobial film 10 may be removed by an application of a second minimum frictional force that is less than the first minimum frictional force. In some embodiments, the second minimum frictional force is equal to or less than a moderate frictional force applied by a wiping motion with wipe article 18.

In some embodiments, as shown in FIG. 3, remover composition 14 may be impregnated within wipe article 18. In this embodiment, the user may forgo a separate step of depositing remover composition 14 onto antimicrobial film 10. As the user applies frictional force to antimicrobial film 10 with wipe article 18, remover composition 14 is extracted from wipe article 18 and deposits onto antimicrobial film 10. Remover composition 14 then dissolves and/or swells the polymer in the film-forming composition of antimicrobial film 10, thereby allowing antimicrobial film 10 to be wiped away from surface 12 after several strokes with wipe article 18. Accordingly, wipe article 18 is a disposable article that reduces time and effort the user must undertake to remove antimicrobial film 10 from surface 12.

After antimicrobial film 10 is removed from surface 12, a fresh coating of antimicrobial film 10 may be coated on surface 12, pursuant to the coating techniques discussed above in FIG. 1. This may provide antimicrobial protection to surface 12 for extended periods of time. For example, when substantially all of the antimicrobial agents are released from a first coating of antimicrobial film 10, a user may deposit remover composition 14 on antimicrobial film 10, and wipe the first coating of antimicrobial film 10 away. The user may then coat surface 12 with a second coating of antimicrobial film 10 to provide a renewed source of protection against microbial contamination.

EXAMPLES

The present invention is more particularly described in the following examples that are intended to be illustrative and not limiting, since numerous modifications and variations within the scope of the present invention will be apparent to those skilled in the art. Examples 1-20 are working examples, and Examples 21-27 are prophetic examples.

Unless otherwise noted, all parts, percentages, and ratios reported in the following examples are on a weight basis, and all reagents used in the examples were obtained, or are available, from the chemical suppliers described below, or may be synthesized by conventional techniques.

The following compositional abbreviations are used in the following Examples:

| | |
|---|---|
| "AgION": | A silver-containing inorganic zeolite food-grade antimicrobial agent, type AJ, which contains 2.5% silver, and which is commercially available under the trade designation "AgION" Antimicrobial from AgION Technologies, Inc., Wakefield, MA. |
| "Triclosan": | Triclosan antimicrobial agent, commercially available from Ciba Specialty Chemicals., Tarrytown, NY. |
| "Lauricidin solution": | A fluid solution containing 20.0% glycerol monolaurate fatty acid monoester (commercially available under the trade designation "LAURICIDIN" from Med-Chem Laboratories, East Lansing, MI), 10.0% 2-hydroxybenzoic (salicylic) acid ($HOC_6H_8CO_2H$) with a formula weight of 138.1 (commercially available from Sigma-Aldrich Chemical Company, Saint Louis, MO), and 10.0% dioctylsulfosuccinate (DOSS) surfactant (commercially available from Alfa Aesar, Ward Hill, MA) in isopropanol. |
| "Bardac 205M": | A quaternary ammonium compound commercially available under the trade designation "BARDAC 205M" from Lonza Group Ltd., Valais, Switzerland. . |
| "Bardac 208M": | A quaternary ammonium compound commercially available under the trade designation "BARDAC 208M" from Lonza Lonza Group Ltd., Valais, Switzerland. |
| "Zn Pyrithione": | Zinc pyrithione, which is synthesized from 2-mercaptopyridine N-oxide salt and zinc acetate, both of which are commercially available from Sigma-Aldrich Chemical Company, Saint Louis, MO. |
| "Silver oxide": | Silver oxide (AgO) having a formula weight of 123.9, commercially available from Alfa Aesar, Ward Hill, MA. |
| "Vantocil P": | A poly(iminoimidocarbonylimidocarbonylimino-hexamethylene hydrochloride), pH 5-6, 20% by weight active in water, commercially available under the trade designation "VANTOCIL P" from Arch Chemicals, Inc., Norwalk, CT. |
| "Vantocil IB": | A poly(iminoimidocarbonylimidocarbonylimino-hexamethylene hydrochloride), pH 4-5, 20% by weight active in water, commercially available under the trade designation "VANTOCIL IB" from Arch Chemicals, Inc., Norwalk, CT. |

-continued

| | |
|---|---|
| "Metasol TK 25": | A thiabendazole-based agent, commercially available under the trade designation "METASOL TK 25" from Lanxess Corporation, Pittsburgh, PA. |
| "AgION SilverClene 24": | A silver-containing inorganic zeolite food-grade antimicrobial agent, which contains 0.003% silver, 4.8% citric acid, and which is commercially available under the trade designation "AGION SILVERCLENE 24" Antimicrobial from AgION Technologies, Inc., Wakefield, MA. |
| "CHG": | 20% chlorhexidine gluconate by weight in water, commercially available from Xttrium Laboratories, Inc., Chicago, IL. |
| "Ammonium Carbonate": | Ammonium carbonate salt, commercially available from Sigma-Aldrich, Milwaukee, WI. |
| "PVOH": | A polyvinyl alcohol polymer with molecular weight of 180,000 Daltons, commercially available from Sigma-Aldrich Chemical Company, Saint Louis, MO. |
| "PVP-K90": | A polyvinylpyrrolidone polymer with molecular weight of 90,000 Daltons, which is commercially available under the trade designation "PVP-K90" from Peakchem, ZheJiang, China. |
| "R-960": | A water based urethane dispersion containing 33% solids, commercially available under the trade designation "NEOREZ R-960" from DSM-NeoResins, Wilmington, MA. |
| "RU21-075": | A water-based polyurethane dispersion containing 40% solids, commercially available under the trade designation "RU21-075" from Stahl USA, Peabody, MA. |
| "Sancure 815": | A water-based polyurethane dispersion, commercially available under the trade designation "SANCURE 815" from Noveon, Inc., Cleveland, OH. |
| "PVP": | A polyvinylpyrrolidone (2% solids in water), commercially available under the trade designation "K-12" from International Specialty Products, Wayne, NJ. |
| "Incorez 835/494": | A soft aliphatic polyurethane dispersion (5% in water), commercially available under the trade designation "INCOREZ 835/494" from Industrial Copolymers, Ltd., Lancashire, England. |
| "Incorez 835/140": | A hard aliphatic polyurethane dispersion (5% in water), commercially available under the trade designation "INCOREZ 835/140" from Industrial Copolymers, Ltd., Lancashire, England. |
| "Cydrothane HP 5035": | A hard aromatic polyurethane dispersion (5% in water), commercially available under the trade designation "CYDROTHANE HP 5035" from Cytek Industries, Inc., West Paterson, NJ |
| "Cydrothane HP 1035": | A soft aromatic polyurethane dispersion (5% in water), commercially available under the trade designation "CYDROTHANE HP 1035" from Cytek Industries, Inc., West Paterson, NJ |
| "GlossTek": | A reactive aliphatic polyurethane, commercially available under the trade designation "GLOSSTEK" from Ecolab, St. Paul, MN. |
| "Stance": | A zinc cross-linked acrylic plus polyethylene wax dispersion, commercially available under the trade designation "STANCE" from 3M Corporation, St. Paul, MN. |
| "Cornerstone": | An acrylic floor sealer/finish (25% in water), commercially available under the trade designation "CORNERSTONE" from 3M Corporation, St. Paul, MN. |
| "NeoCryl XK-98": | A self cross-linking acrylic dispersion commercially available under the trade designation "NEOCRYL XK-98" from DSM NeoResins, Wilmington, MA. |
| "B66 acrylic resin": | An acrylic resin commercially available under the trade designation "SPEC-CRETE SUPERSEAL B66" from Farfari & Mendes Ltd., Georgetown, Guyana. |
| "XK-90": | A 40% acrylic cross-linkable polymer dispersion in water, commercially available under the trade designation "NEOPAC XK-90" from DSM-NeoResins, Wilmington, MA. |
| "XR-2500": | A polyfunctional aziridine cross-linker commercially available under the trade designation "XR-2500" from Stahl USA, Peabody, MA. |

-continued

| | |
|---|---|
| "XL-A": | A combination of 76 parts ethanol, 22.8 parts of an aziridine cross-linker commercially available under the trade designation "CX-100" from DSM NeoResins, Wilmington, MA, arid 1.2 parts of a surfactant commercially available under the trade designation "SURFYNOL 104PA" from Air Products and Chemicals, Inc. Allentown, PA. The combined mixture was blended for 20 minutes under high shear. |
| "Exxate 800": | An oxo-alkyl acetic ester solvent commercially available under the trade designation "EXXATE 800" from Exxon Mobil Corporation, Houston, TX. |
| "PET film": | A polyethylene terephthalate film with acrylate-primed layer, commercially available from Mitsubishi, Japan. |
| "BOPP Film": | A biaxially-oriented, corona-treated, polypropylene film available from 3M Corporation, St. Paul, MN. |

Examples 1 and 2

Antimicrobial films of Examples 1 and 2 were each prepared pursuant to the following procedure. A PVOH solution was prepared by combining 5 parts of PVOH with 95 parts water, and shaking the mixture in a warm bath for 24 hours to fully dissolve the PVOH. 30 parts of the PVOH solution were then mixed with 0.2 parts of an antimicrobial agent (AgION for Example 1, and Triclosan for Example 2). The resulting film-forming composition was then coated onto a corona-treated BOPP film using a Meyer rod #36, and dried at 55° C. for 5 minutes to form the antimicrobial film.

The antimicrobial films of Examples 1 and 2 were each tested for "microbial load reduction" pursuant to ASTM E2180-01, which involved inoculation of a molten (45° C.) agar slurry with a standardized culture of bacterial cells. A thin layer of the inoculated agar slurry (0.5 milliliter) was then pipetted onto the test material and the untreated control material. Samples were tested in duplicate using *Staphylococcus aureus* (ATCC 6538) and *Pseudomonas aeruginosa* (ATCC 9027). After 24 hours, surviving microorganisms were recovered via elution of the agar slurry inoculum from the test substrate into DIE Neutralizing broth and extracted by sonication and vortexing. Serial dilutions were then made, and pour plates were made of each dilution. Agar plates were incubated for 48 hours at 28° C.±1° C. Bacterial colonies from each dilution series were then counted and recorded. Calculation of percent reduction of bacteria from treated versus untreated samples was then made. A percent reduction greater than 99.95% was reported as 100%.

Table 1 provides the microbial load reduction results for the antimicrobial films of Examples 1 and 2.

TABLE 1

| Example | Antimicrobial Agent | % Reduction *S. aureus* (Gram Positive) | % Reduction *Ps. aeruginosa* (Gram Negative) |
|---|---|---|---|
| Example 1 | AgION | 100 | 100 |
| Example 2 | Triclosan | 100 | 0 |

The results shown in Table 1 illustrate the good antimicrobial activity provided by the antimicrobial films of Examples 1 and 2. The antimicrobial film of Example 2 exhibited poor gram negative results, which is typical for Triclosan antimicrobial agents.

The antimicrobial films of Examples 1 and 2 were also tested for ease of removal with a remover composition. Synthetic wipes (commercially available under the trade designation "TX1009 ALPHAIPE" from ITW Texwipe, Upper Saddle River, N.J.) were used for the evaluation. For each antimicrobial film, a 4"×4" piece of a synthetic wipe was saturated with water at room temperature and rubbed over the antimicrobial film. For each antimicrobial film of Examples 1 and 2, the film was removed from the BOPP substrate after two strokes with the wet synthetic wipe. Based on visual observations, the first stroke appeared to wet and soften the antimicrobial film due to the antimicrobial film swelling, and the second stroke removed it in a solid form. This demonstrates that the antimicrobial film was swelled by water but did not dissolve in water and was durable enough to substantially withstand dissolution in water due to the relatively high molecular weight of PVOH that was used.

Examples 3-8

Antimicrobial films of Examples 3-8 were each prepared pursuant to the following procedure. A solution was prepared by dissolving PVP-K90 and an antimicrobial agent in a 50:50 solution of isopropanol and methyl ethyl ketone. The solution was then coated on a non-treated polyethylene terephthalate substrate using a Meyer rod #9. The coated film was dried at room temperature for 20 minutes and then dried at 80° C. for 10 minutes.

The antimicrobial films of Examples 3-8 were each tested for "microbial load reduction" pursuant to the procedure discussed above for Examples 1 and 2. A control coating of PVP-K90 without an antimicrobial agent was used as a control.

TABLE 2

| Example | Antimicrobial Agent | Percent by Weight of Antimicrobial Agent | % Reduction *S. aureus* (Gram Positive) | % Reduction *Ps. aeruginosa* (Gram Negative) |
|---|---|---|---|---|
| Example 3 | Lauricidin solution | 6 | 100 | 0 |
| Example 4 | Bardac 208M | 6 | 100 | 100 |
| Example 5 | Bardac 205M | 6 | 100 | 100 |
| Example 6 | Triclosan | 6 | 100 | 0 |
| Example 7 | AgION | 5 | 100 | 100 |
| Example 8 | Zn Pyrithione | 6 | 83.8 | 97.7 |

The results shown in Table 2 illustrate the good antimicrobial activity provided by the antimicrobial films of Examples 3-8. Accordingly, a variety of antimicrobial agents may be used with the present invention.

Examples 9-15 and Comparative Examples A and B

Antimicrobial films of Examples 9-15 and Comparative Examples A and B were each prepared pursuant to the following procedure. A solution was prepared by combining an antimicrobial agent, a cross-linking agent, a polymer dispersion, and 5 parts of water. For the films of Examples 9-11 and Comparative Example A, the polymer dispersion was 20 parts of R-960, and for the films of Examples 12-15 and Comparative Example B, the polymer dispersion was 10 parts of RU21-075. Table 3 provides the antimicrobial agents and cross-linking agents combined in the solutions for the films of Examples 9-15 and Comparative Examples A and B.

TABLE 3

| Example | Antimicrobial Agent | Parts of Antimicrobial Agent | Cross-Linker | Parts of Cross-Linker |
|---|---|---|---|---|
| Comparative Example A | None | 0.0 | None | 0.0 |
| Example 9 | AgION | 0.5 | XR-2500 | 0.2 |
| Example 10 | AgION | 0.5 | XL-A | 4.0 |
| Example 11 | Triclosan | 5.0 | XL-A | 4.0 |
| Comparative Example B | None | 0.0 | None | 0.0 |
| Example 12 | AgION | 0.5 | XL-A | 2.0 |
| Example 13 | AgION | 0.5 | XR-2500 | 0.1 |
| Example 14 | Triclosan | 1.0 | XL-A | 2.0 |
| Example 15 | Triclosan | 1.0 | XR-2500 | 0.1 |

The resulting film-forming compositions were then coated onto a corona-treated BOPP film using a Meyer rod #6, and dried at 55° C. for 5 minutes to form the antimicrobial film. The antimicrobial films of Examples 9-15 and Comparative Examples A and B were then each tested for "microbial load reduction" pursuant to ASTM E2180-01, as discussed above for Examples 1 and 2. Table 4 provides the microbial load reduction results for the antimicrobial films of Examples 9-15 and Comparative Examples A and B.

TABLE 4

| Example | Antimicrobial Agent | Parts of Antimicrobial Agent | % Reduction S. aureus (Gram Positive) | % Reduction Ps. aeruginosa (Gram Negative) |
|---|---|---|---|---|
| Comparative Example A | None | 0.0 | 0.0 | 0.0 |
| Example 9 | AgION | 0.5 | 99.7 | 100.0 |
| Example 10 | AgION | 0.5 | 99.4 | 100.0 |
| Example 11 | Triclosan | 5.0 | 69.7 | 0.0 |
| Comparative Example B | None | 0.0 | 0.0 | 0.0 |
| Example 12 | AgION | 0.5 | 98.9 | 100.0 |
| Example 13 | AgION | 0.5 | 96.0 | 100.0 |
| Example 14 | Triclosan | 1.0 | 89.0 | 0.0 |
| Example 15 | Triclosan | 1.0 | 41.0 | 19.0 |

The results shown in Table 4 further illustrate the good antimicrobial activity provided by the antimicrobial films of the present invention. As discussed above, the antimicrobial films containing Triclosan (i.e., Examples 11, 14, and 15) exhibited poor gram negative results, which is typical for Triclosan antimicrobial agents. In addition, the antimicrobial films containing Triclosan exhibited relatively poor gram positive results. This could be due to the triclosan interacting more strongly with the polymer of the antimicrobial film.

The antimicrobial films of Examples 9, 10, 12, and 13, and Comparative Examples A and B were also tested for ease of removal from the BOPP film with a remover composition pursuant to the following procedure. Each sample was sprayed with WINDEX-brand glass cleaner solution., which is commercially available from SC Johnson & Son, Inc., Racine, Wis. After a 30 second waiting period, the sample was then wiped three strokes under moderate force with a paper towel, and the amounts of the film removed were estimated by visual observation. Table 5 provides the percent removal for the antimicrobial films of Examples 9, 10, 12, and 13, and Comparative Examples A and B.

TABLE 5

| Example | Polymer Matrix Material | Cross-Linker | % Removal |
|---|---|---|---|
| Comparative Example A | R-960 | None | 100% |
| Example 9 | R-960 | XR-2500 | 10 |
| Example 10 | R-960 | XL-A | 10 |
| Comparative Example B | RU21-075 | None | 100 |
| Example 12 | RU21-075 | XL-A | 100 |
| Example 13 | RU21-075 | XR-2500 | 90 |

The results shown in Table 5 illustrate the difference in removal based on the type of cross-linked polymer dispersion used. This is shown by the films of Examples 9 and 10, which used the R-960. Accordingly, a stronger solvent is more desirable for use with the films of Examples 9 and 10. In comparison, however, the films of Examples 12 and 13 exhibited low resistances to the alkali environment, and were readily removed. As such, ammonia-based solvents are suitable as remover compositions for antimicrobial films containing cross-linked RU21-075 polymer matrix materials.

Example 16

An antimicrobial film of Example 16, which is an example of a self cross-linking polymer, was prepared pursuant to the following procedure. A mixture was formed by combining 95 parts of NeoCryl XK-98 with 5 parts AgION. The mixture was then coated onto BOPP film using a Meyer rod #14 and dried in an oven at 60° C. for 5 minutes. While drying, the NeoCryl XK-98 polymer self cross-linked via a condensation reaction. The resulting antimicrobial film of Example 16 was then tested for "microbial load reduction" pursuant to ASTM E2180-01, as discussed above for Examples 1 and 2. The film of Example 16 exhibited a 100% microbial load reduction for both S. aureus (gram positive) and Ps. aeruginosa (gram negative).

The antimicrobial film of Example 16 was also tested for ease of removal from the BOPP film with remover compositions. A first sample of the film was sprayed with water and a second sample of the film was sprayed with WINDEX-brand glass cleaner solution, which is commercially available from SC Johnson & Son, Inc., Racine, Wis. After a 30 second waiting period, the samples were then wiped three strokes under moderate force with a paper towel, and the amount of the film removed was observed. For the water-sprayed sample, the film was unaffected by the water and was not removed. This is due to the cross-linked structure of the film. In contrast, for the WINDEX-sprayed sample, the film was readily removed. As a result, the antimicrobial film of Example 16 is suitable for use on a variety of surfaces that are treated with water. The cross-linked polymer matrix prevents the antimicrobial film of Example 16 from being removed during normal washing operations (e.g., washing a surface with a wetted towel or sponge), but is readily removed when a WINDEX-based remover composition is applied.

Example 17

An antimicrobial film of Example 17, which is an example of AgION silver in a solvent-borne formulation, was prepared pursuant to the following procedure. A mixture was prepared by combining 2 parts by weight of B66 acrylic resin, 0.2 parts AgION, and 8 parts Exxate 800 solvent. The mixture was stirred for one hour to dissolve the B66 acrylic resin and disperse the AgION. The resulting mixture was then coated on a BOPP film using a Meyer rod #26. The film was then dried in an oven at 55° C. for 5 minutes. The coating appearance was transparent, but non-uniform with a blotchy surface.

The resulting antimicrobial film of Example 17 was then tested for "microbial load reduction" pursuant to ASTM E2180-01, as discussed above for Examples 1 and 2. The film of Example 17 exhibited a 68.4% microbial load reduction for *S. aureus* (gram positive) and a 100.0% microbial load reduction for *Ps. aeruginosa* (gram negative). Additionally, a wipe was saturated with MEK (methyl ethyl ketone) and used to rub the film. After three strokes, about 80% of the film was removed, as estimated by visual observation.

Example 18

An antimicrobial film of Example 18, which is an example of AgION silver in a water-based formulation, was prepared pursuant to the following procedure. A mixture was prepared by combining 8.6 parts XK-90 (acrylic cross-linkable polymer dispersion in water), 0.6 parts XL-A cross-linker, and 0.4 parts AgION. The mixture was stirred for a few minutes until homogeneous in appearance. The composition was coated onto a BOPP film using a Meyer rod #14. The film was then dried at 55° C. for 5 minutes. The resulting film appearance was hazy, but uniform.

The resulting antimicrobial film of Example 18 was then tested for "microbial load reduction" pursuant to ASTM E2180-01, as discussed above for Examples 1 and 2. The film of Example 17 exhibited a 100.0% microbial load reduction for both *S. aureus* (gram positive) and *Ps. aeruginosa* (gram negative).

To assess the ease of film removal, a spray of water, WINDEX-brand glass cleaner solution, soapy warm water, and MEK were applied to the film. After allowing each solvent to interact with the film for 10 minutes, the film plus solvent was wiped using a KemWipe and applying moderate force. The film was unaffected under the areas saturated with water, WINDEX-brand glass cleaner solution, and soapy warm water.

Most of the film was removed under the area saturated with MEK. This shows that the film-forming composition in this example exhibits high durability and requires an aggressive solvent for the remover composition.

Example 19

An antimicrobial film of Example 19 was prepared pursuant to the following procedure. A silver oxide solution was initially prepared by combining 5 parts ammonium carbonate salt with 95 parts water, and mixing until the salt was dissolved. To this solution, 1 part silver oxide was added. The mixture was stirred at 60° C. for one hour until the silver oxide was dissolved. A mixture was then prepared by combining 20 parts by weight of XK-90 binder material, 1 part silver oxide solution, 2 parts XL-A cross-linker, and 12 parts water. The mixture was shaken by hand to form a uniform dispersion, and then coated on a PET film using a Meyer rod #12. The film was then dried at in an oven at 55° C. for 5 minutes and cured. The resulting film appearance was transparent and uniform, with a slight brown tint due to the presence of the silver oxide. This color tint can be beneficial for allowing a user to visually determine the presence and uniformity of the coating.

The resulting antimicrobial film of Example 10 was then tested for "microbial load reduction" pursuant to ASTM E2180-01, as discussed above for Examples 1 and 2. The film of Example 28 exhibited a 51.2% microbial load reduction for *S. aureus* (gram positive) and a 100.0% microbial load reduction for *Ps. aeruginosa* (gram negative).

Example 20

An antimicrobial film of Example 20, which included a fast-acting antimicrobial agent, was prepared pursuant to the following procedure. A solvent of 60 parts ethyl alcohol and 40 parts water was initially prepared. A mixture was then prepared by adding 6 parts PVOH polymer to the solvent. The mixture was shaken in warm bath until the PVOH was dissolved, which was about 24 hours. After the shaking process, 1 part AgION was added to the mixture. The resulting mixture exhibited instant bacterial kill capabilities due to the high content of ethyl alcohol, while the coated composition also provided for longer-term antimicrobial activity after the alcohol evaporates as shown above in Example 1. This illustrates the versatility of the present invention for reducing pathogen contamination.

Examples 21-27

Examples 21-27 illustrate prophetic polymer-antimicrobial agent combinations that can be used to form water-insoluble, biocidal antimicrobial films according to the present invention. Table 6 provides the listing of the polymer-antimicrobial agent combinations for Examples 21-27. For each of Examples 21-27, a plurality of antimicrobial agents can be used alone or in combination and are listed in a comma-delimited manner to signify this. The following letter codes are used to abbreviate the antimicrobial agents in Table 6: A=Vantocil IB, B=Triclosan, C=AgION SilverClene 24, and D=CHG.

TABLE 6

| Example | Polymer | Antimicrobial Agent |
| --- | --- | --- |
| Example 21 | Cornerstone (25% in water) | A, B, C, D |
| Example 22 | Incorez 835/494 (5% in water) | C, D |

TABLE 6-continued

| Example | Polymer | Antimicrobial Agent |
|---|---|---|
| Example 23 | Incorez 835/140 (5% in water) | C, D |
| Example 24 | Cydrothane HP 5035 (5% in water) | C, D |
| Example 25 | Cydrothane HP 1035 (5% in water) | C, D |
| Example 26 | GlossTek | C, D |
| Example 27 | Stance | A, B, C, D |

The embodiments described above and illustrated in the figures are presented by way of example only and are not intended as a limitation upon the concepts and principles of the present invention. As such, it will be appreciated by one having ordinary skill in the art that various changes in form and detail are possible without departing from the spirit and scope of the present invention. Various features and aspects of the invention are set forth in the following claims.

The invention claimed is:

1. An antimicrobial coating system comprising:
a film-forming composition comprising
a polymer having an effective molecular weight, such that a film formed from the film-forming composition is water-insoluble, and
an effective amount of an antimicrobial agent dispersed within the polymer, and
an indicator dye that provides color to the composition when wet and is colorless when dry;
the film-forming composition forming a water-insoluble, biocidal antimicrobial film when applied to a surface.

2. The antimicrobial coating system of claim 1, further comprising a remover composition comprising a solvent capable of dissolving or swelling the film-forming composition.

3. The antimicrobial coating system of claim 2, wherein the polymer exhibits a first Hildebrand solubility parameter, the solvent exhibits a second Hildebrand solubility parameter, and the difference between the first Hildebrand solubility parameter and the second Hildebrand solubility parameter is $5.0 \, (\text{cal/cm}^3)^{1/2}$ or less.

4. The antimicrobial coating system of claim 2, wherein Gibbs free energy of mixing between the polymer and the solvent is a negative value.

5. The antimicrobial coating system of claim 1, wherein the antimicrobial film exhibits microbial load reductions of at least about 99% for gram positive pathogens or gram negative pathogens, when tested pursuant to ASTM E2180-01.

6. The antimicrobial coating system of claim 1, wherein the antimicrobial film exhibits microbial load reductions of at least about 99% for gram positive pathogens and gram negative pathogens, when tested pursuant to ASTM E2180-01.

7. The antimicrobial coating system of claim 1, wherein the polymer constitutes about 90% by weight to about 99% by weight of the film-forming composition, and wherein the antimicrobial agent constitutes about 1% by weight to about 10% by weight of the film-forming composition.

8. The antimicrobial coating system of claim 1, wherein the film-forming composition further comprises a fast-acting antimicrobial agent selected from the group consisting of quaternary ammonium salts, benzalkonium chlorides, biguanide compounds, alcohols, bleach, hydrogen peroxide, urea hydrogen peroxide, hydrogen peroxide stabilized in a sodium pyrophosphate matrix, hydrogen peroxide chelated in polyvinylpyrrolidone, and combinations thereof.

9. The antimicrobial coating system of claim 1, wherein the film-forming composition further comprises a cross-linking agent.

10. The antimicrobial coating system of claim 1, wherein the polymer comprises a cross-linkable polymer composition.

11. The antimicrobial coating system of claim 1, wherein the polymer comprises a water-soluble polymer composition comprising at least one of polyvinyl alcohol, polyvinylpyrrolidone, and combinations thereof.

12. The antimicrobial coating system of claim 1, wherein the polymer comprises at least one of polyvinyl alcohol having an effective molecular weight, acrylic, urethane, and combinations thereof.

13. The antimicrobial coating system of claim 1, wherein the antimicrobial agent comprises at least one of a fatty acid monoester, a fatty acid monoether, a transition metal ion-containing compound, a quaternary ammonium-containing compound, a biguanide, and a combination thereof.

14. The antimicrobial coating system of claim 1, wherein the polymer comprises a polyvinylpyrrolidone, and the antimicrobial agent comprises at least one of a glycerol monolaurate fatty acid monoester, a quaternary ammonium compound, a silver-containing compound, a zinc pyrithione, and combinations thereof.

15. The antimicrobial coating system of claim 1, wherein the polymer comprises at least one of a polyurethane and a cross-linkable acrylic dispersion, and the antimicrobial agent comprises a silver-containing compound.

16. A wipe article comprising the antimicrobial coating system of claim 1 impregnated therein.

17. A method for verifying the presence of an antimicrobial film, the method comprising:
applying the film-forming composition of claim 1 to a surface, using the color of the indicator dye to visually verify coverage;
drying the film-forming composition to form a water-insoluble, biocidal antimicrobial film, the resulting, dry antimicrobial film being colorless;
wetting the surface; and
based on whether a color change occurred upon wetting the surface, determining whether the antimicrobial film is still intact on the surface.

18. A method for verifying the presence of an antimicrobial film, the method comprising:
applying the film-forming composition of claim 1 to a surface, using the color of the indicator dye to visually verify coverage;
drying the film-forming composition to form a colorless water-insoluble, biocidal antimicrobial film;
applying a substance to which the indicator dye is sensitive; and
based on whether a color change occurred upon applying the substance to the surface, determining whether the antimicrobial film is still intact on the surface.

19. A method of verifying the presence of an antimicrobial film, the method comprising:
providing an antimicrobial film applied to a surface, the antimicrobial film comprising
a polymer having an effective molecular weight, such that the antimicrobial film is water-insoluble,
an effective amount of an antimicrobial agent, such that the antimicrobial film is biocidal, and
an indicator dye that is colorless when dry and provides color when wet;
when dry and provides color when wet;
wetting the surface; and
based on whether a color change occurred upon wetting the surface, determining whether the antimicrobial film is still intact on the surface.

* * * * *

UNITED STATES PATENT AND TRADEMARK OFFICE
CERTIFICATE OF CORRECTION

| | | |
|---|---|---|
| PATENT NO. | : 8,124,169 B2 | |
| APPLICATION NO. | : 12/097334 | |
| DATED | : February 28, 2012 | |
| INVENTOR(S) | : Caroline M. Ylitalo | |

It is certified that error appears in the above-identified patent and that said Letters Patent is hereby corrected as shown below:

Column 3
Line 17, Delete "11," and insert -- 10, --, therefor.

Column 4
Line 51, Delete "NeoResins," and insert -- NeoResins. --, therefor.

Column 5
Line 10, Delete ""XR-2500)"" and insert -- "XR-2500" --, therefor.

Column 6
Line 62, Delete "napthenate)," and insert -- naphthenate), --, therefor.

Column 7
Line 15, Delete "monolaurate" and insert -- monolaurate, --, therefor.
Line 17, Delete "Uniquema" and insert -- Uniqema --, therefor.
Line 26, Delete "monethers," and insert -- monoethers, --, therefor.

Column 13
Line 62, Delete "$\Omega_1$" and insert -- $\chi_1$ --, therefor.
Line 64, Delete "E. G.," and insert -- e.g., --, therefor.

Column 15
Line 48, Delete "Switzerland. ." and insert -- Switzerland. --, therefor.
Line 50, After "from" delete "Lonza".

Column 16
Line 42, Delete "NJ" and insert -- NJ. --, therefor.
Line 46, Delete "NJ" and insert -- NJ. --, therefor.
Line 60, Delete "Farfari" and insert -- Farfan --, therefor.

Signed and Sealed this
Twenty-ninth Day of May, 2012

David J. Kappos
*Director of the United States Patent and Trademark Office*

CERTIFICATE OF CORRECTION (continued)
U.S. Pat. No. 8,124,169 B2

Column 17
Line 42, Delete "DIE" and insert -- D/E --, therefor.

Column 18
Line 20, Delete "ALPHAIPE"" and insert -- ALPHAWIPE" --, therefor.

Column 21
Line 64, Delete "KemWipe" and insert -- KimWipe --, therefor.

Column 22
Line 1 -4, Delete "Most of the film was removed under the area saturated with MEK. This shows that the film-forming composition in this example exhibits high durability and requires an aggressive solvent for the remover composition." and insert the same on Col. 21, Line 67, after "water." as a continuation of the Paragraph.

Column 24
Line 46-47, In Claim 18, delete "sensitive;" and insert -- sensitive to the surface; --, therefor.
Line 60, In Claim 19, below "color when wet;" delete "when dry and provides color when wet;".